(12) United States Patent
Schillberg et al.

(10) Patent No.: US 11,718,843 B2
(45) Date of Patent: Aug. 8, 2023

(54) LIGHT-INDUCIBLE TARGETED MODIFICATION OF NUCLEIC ACIDS AND GENETIC INFORMATION

(71) Applicant: Fraunhofer-Gesellschaft zur Foerderung der angewandten Forschung e.V., Munich (DE)

(72) Inventors: Stefan Schillberg, Aachen (DE); Gerda Noelke, Aachen (DE); Stefano Di Fiore, Neuss (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 268 days.

(21) Appl. No.: 16/772,028

(22) PCT Filed: Dec. 19, 2018

(86) PCT No.: PCT/EP2018/085860
§ 371 (c)(1),
(2) Date: Jun. 11, 2020

(87) PCT Pub. No.: WO2019/121928
PCT Pub. Date: Jun. 27, 2019

(65) Prior Publication Data
US 2021/0214710 A1 Jul. 15, 2021

(30) Foreign Application Priority Data
Dec. 20, 2017 (EP) .................. 17208812

(51) Int. Cl.
*C12N 15/01* (2006.01)
*C12N 13/00* (2006.01)
*G01N 21/64* (2006.01)
*C12N 15/10* (2006.01)

(52) U.S. Cl.
CPC ............ *C12N 13/00* (2013.01); *C12N 15/01* (2013.01); *C12N 15/102* (2013.01); *C12Q 2523/313* (2013.01)

(58) Field of Classification Search
CPC ... C12Q 2523/313; C12N 15/02; C12N 13/00
See application file for complete search history.

(56) References Cited

U.S. PATENT DOCUMENTS

| 2005/0026146 A1 | 2/2005 | Frizsche et al. |
| 2011/0212540 A1 | 9/2011 | Yeh et al. |

FOREIGN PATENT DOCUMENTS

| CN | 106018366 A | 10/2016 |
| CN | 106399367 A | 2/2017 |

OTHER PUBLICATIONS

Shamsi et al., Journal of Photochemistry &Photobiolgy B:Biology, 136, 1-11, 2014.*
Zheng et al. "Radiosensitization of DNA by Gold Nanoparticles Irradiated with High-Energy Electrons", Radiation Research, 2008, 169:19-27.
Liang et al. "RGD Peptide-Modified Fluorescent Gold Nanoclusters as Highly Efficient Tumor-Targeted Radiotherapy Sensitizers", Biomaterials, Aug. 16, 2017, 144(2017):95-104.
Jinek et al. "A Programmable Dual-RNA-Guided DNA Endonuclease in Adaptive Bacterial Immunity", Science, Aug. 17, 2012, 337(6096):816-821.
PCT/EP2018/085860 International Search Report and Written Opinion dated Feb. 12, 2019.
Liu et al. "Label-Free and Fluorescence Tum-On Aptasensor for Protein Detection via Target-Induced Silver Nanoclusters Formation", Analytica Chimica Acta, 2012, 749:70-74.
Goswami et al. "Bio-NCs—The Marriage of Ultrasmall Metal Nanoclusters with Biomolecules", Nanoscale, 2014, 6:13328-13347.
Moshnikov V. A. et al., From laser optical microscopy to high resolution fluorescence microscopy. Colloidal quantum dots-biomarkers in exploratory scientific research, Biotechnosphere [in Russian], 2014, No. 6 (36), pp. 16-30.
Search Report for RU 2020123685 dated Feb. 3, 2022.
Office Action dated Mar. 15, 2023 for copending Chinese Patent Application No. 201880082824.4.

* cited by examiner

*Primary Examiner* — Maryam Monshipouri
(74) *Attorney, Agent, or Firm* — Wagenknecht IP Law Group PC

(57) ABSTRACT

The technology provided herein pertains to methods for the modification of a target nucleic acid in vitro, ex vivo or in vivo in the genome of a cell by using a pre-assembled complex comprising a nucleic acid and a metal nanocluster and exposing the complex bound to a target nucleic acid to electromagnetic radiation.

5 Claims, 7 Drawing Sheets

Specification includes a Sequence Listing.

FIGURE 7

A) SEQ ID NO. 12 – eyfp gene (5' → 3')

GTGAGCAAGGGCGAGGAGCTGTTCACCGGGGTGGTGCCCATCCTGGTCGAGCTGGACGGCGACGTAAACGG
CCACAAGTTCAGCGTGTCCGGCGAGGGCGAGGGCGATGCCACCTACGGCAAGCTGACCCTGAAGTTCATCTG
CACCACCGGCAAGCTGCCCGTGCCCTGGCCCACCCTCGTGACCACCTTCGGCTACGGCCTGCAGTGCTTCGCCC
GCTACCCCGACCACATGAAGCAGCACGACTTCTTCAAGTCCGCCATGCCCGAAGGCTACGTCCAGGAGCGCAC
CATCTTCTTCAAGGACGACGGCAACTACAAGACCCGCGCCGAGGTGAAGTTCGAGGGCGACACCCTGGTGAA
CCGCATCGAGCTGAAGGGCATCGACTTCAAGGAGGACGGCAACATCCTGGGGCACAAGCTGGAGTACAACTA
CAACAGCCACAACGTCTATATCATGGCCGACAAGCAGAAGAACGGCATCAAGGTGAACTTCAAGATCCGCCAC
AACATCGAGGACGGCAGCGTGCAGCTCGCCGACCACTACCAGCAGAACACCCCCATCGGCGACGGCCCCGTG
CTGCTGCCCGACAACCACTACCTGAGCTACCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACAAGTAATAA

B) SEQ ID NO. 13– Fragment of the eyfp gene (5' → 3')

365    GCA TCG AGC TGA AGG GCA TCG ACT TCA AGG AGG ACG GCA ACA TCC TGG GGC AC*A AGC TGG AGT ACA ACT ACA ACA GCC ACA ACG TCT ATA TCA T*GG CCG ACA AGC AGA AGA ACG GC*A TCA AGG TGA ACT TCA AGA T*CC GCC ACA ACA TCG   514

LIGHT-INDUCIBLE TARGETED MODIFICATION OF NUCLEIC ACIDS AND GENETIC INFORMATION

CROSS REFERENCE TO RELATED APPLICATIONS

This is a US national phase application under 35 USC § 371 of international patent application no. PCT/EP2018/085860, filed Dec. 19, 2018, which itself claims priority to European application no. 17208812.2, filed Dec. 20, 2017. Each application referred to in this paragraph is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing as file "PCTEP2018085860-2020-06-10-SEQID" created on Jun. 10, 2020, filed on Jun. 11, 2020 and having a size of 4 Kilobytes. The sequence listing contained in this ASCII formatted document forms part of the specification and is herein incorporated by reference in its entirety.

FIELD OF THE DISCLOSURE

The technology provided herein generally falls under the umbrella of genome editing (GE) technologies and pertains to methods for the modification of a target nucleic acid in vitro, ex vivo or in vivo in the genome of a cell by using a pre-assembled complex comprising a nucleic acid and a metal nanocluster and exposing the complex bound to a target nucleic acid to electromagnetic radiation.

BACKGROUND

The variety of traits found in nature reflects the presence of one or multiple mutations in certain genes, which often arise as mistakes in the repair mechanism initiated after DNA damage. To expand the repertoire of traits readily available for breeding, methods for artificially changing genomes by means of mutations induced by chemicals and radiation have been developed. More recently, strategies such as tilling (Targeting Induced Local Lesions in Genomes) have been developed as reverse genetics tools, which also entail the use of a chemical or radiation mutagens, causing extensive DNA damage and therefore, mutations. These classical approach considerably expanded the range of practically useful traits available for breeding and accelerated the establishment and release of improved plant varieties. However, as the mutations are induced randomly, extensive screening efforts to identify the mutation of interest are still needed. In addition, as many mutations are induced simultaneously, after successful identification of a line displaying the desired trait, several rounds of backcrossing are needed to eliminate most of the background mutations. With the discovery of site-directed nucleases (SDNs) and the advent of genome editing it is now possible to induce a break, and therefore a mutation, at specific pre-determined locations in the genome. These locations in the genome are defined by their sequence and the sequence specificity of the DNA-modifying enzymes. In fact, when a double strand break occurs in a higher eukaryotic cell, it is often repaired via the Non-Homologous End Joining (NHEJ) pathway resulting in small insertions or deletions (indels) which mutate the targeted gene. If a short piece of double or single stranded DNA homologous to the targeted region but carrying a single or few base mutations is provided along with the nuclease, the break can be repaired by the Homology-Directed Repair (HDR) pathway, allowing to precisely edit a few nucleotides in the target gene.

Several genome editing (GE) technologies have been recently developed to achieve a controlled modification at predefined sites of the genetic information encoded in the genome of microbes, plants and mammalians. In contrast to classical breeding and traditional approaches for gene transfer, in which the integration of foreign genes or the modification of existing genes occurs in an uncontrolled and random fashion, recent GE technologies (especially those based on so-called designer endonucleases) can target specific genomic sites for modification. The engineered endonucleases generate double strand DNA breaks (DSBs) which are resolved by endogenous DNA repair mechanisms. In animals and plants, the prevalent repair mechanism for DSBs is non-homologous end joining (NHEJ). Although this can restore the original structure and function of the gene, it is an error-prone mechanism that often causes the insertion or deletion of a few nucleotides at the break site, thereby generating missense, nonsense or frameshift mutations that result in the loss of gene function. If donor DNA homologous to the genomic DNA target is introduced at the same time as the designer nuclease, the DSB can instead be processed by homology-dependent repair (HDR) which can restore the original sequence or (if the donor DNA carries mutations or additional genes) result in gene conversion or precise transgene insertion.

The most widely used current GE technologies are based on mega nucleases, zinc finger nucleases (ZNFs), transcription activator-like effector nucleases (TALENs) or clustered regularly interspaced short palindromic repeats (CRISPR/Cas9). An alternative GE method which does not rely on nucleases is oligonucleotide-directed mutagenesis (ODM), which has been commercialized by the company CIBUS. ODM uses single-stranded oligonucleotides as a donor template, and can therefore introduce small insertions and deletions as well as single or clustered nucleotide changes. All these techniques are successfully used in biotechnology for applications such as gene function studies, introduction of novel traits into crops. They are also intensively studied in animal and human cells and tissues for biomedical applications. However, the prolonged activity of meganucleases, ZFNs, TALENs and CRISPR/Cas in plant or animal cells can often result into undesired off-targets effects.

Therefore, more effective and specific ways for GE in vitro, ex vivo or in vivo in the genome of a cell are needed. In particular, the technical problem to be solved is the development of a non-transgenic, protein- and nuclease-free highly specific and efficient method for modification of nucleic acids in vitro and/or in the genome of organisms/cells. Moreover, the present methods aim to reduce/eliminate off-target effects frequently reported in the literature for current GE technologies, by which unexpected and undesired mutations are introduced in the genome of target organisms.

SUMMARY OF THE DISCLOSURE

The present disclosure relates to methods for the modification of a target nucleic acid in vitro, ex vivo or in vivo in the genome of a cell by using a pre-assembled metal-DNA quantum clusters complex (hereafter referred to as QC) comprising a nucleic acid and a metal nanocluster and exposing the QC complex bound to a target nucleic acid to electromagnetic radiation. In the methods of the present disclosure QCs are used as a novel GE tool. QCs are composite molecules assembled in particular from 5-20 metal atoms (e.g. silver or gold) templated by DNA oligonucleotides differing in length and sequence, which in turn may lead to different formats such as linear QCs, stem-loops or hairpins. The synthesis of QCs is simple and inexpensive. In solution with DNA oligonucleotides, metal atoms preferentially bind to cytosine and guanine rather than adenine and thymine, and following their chemical reduction they form clusters while the DNA oligonucleotide folds. The folded QCs have overhanging single-stranded tails that can recognize and bind to target DNA sequences in e.g. the genome of cells, organs or organisms (see FIG. 1).

Thus one aspect of the present disclosure relates to methods for the modification of a target nucleic acid in vitro, ex vivo or in vivo in the genome of a cell comprising:
(i) providing a target nucleic acid sequence to be modified;
(ii) providing a pre-assembled complex comprising a nucleic acid and a metal nanocluster;
(iii) binding the complex to the target nucleic acid;
(iv) inducing one or more single or double stranded nucleic acid breaks in the target nucleic acid by exposing the complex bound to the target nucleic acid to electromagnetic radiation.

Another aspect relates to complexes and methods for modification/editing a target DNA having a nucleotide sequence, wherein the complex used in the methods comprises a nucleotide sequence that binds to a portion of the nucleotide sequence of the DNA target by e.g. hybridization, and a nucleotide sequence that comprises a metal nanocluster, for inducing one or more single or double stranded nucleic acid breaks in the target nucleic acid by exposing the complex bound to the target nucleic acid to electromagnetic radiation.

The disclosed methods have some technical advantages like to reduce or even eliminate off-targets effects which is one of the major drawback of the most popular GE techniques available at present. This is due to the fact that as long as the electromagnetic radiation like light is not hitting the QCs with a specific wavelength, energy and intensity, there is no uncontrolled mutation induced by the QCs. The electromagnetic radiation pulse hitting the QCs should also be kept as short as possible to prevent damage to unwanted regions, of e.g. the genome of the target organism.

Before the disclosure is described in detail, it is to be understood that this disclosure is not limited to the particular aspects of the present disclosure. It is also to be understood that the terminology used herein is for purposes of describing particular aspects only, and is not intended to be limiting. It must be noted that, as used in the specification and the appended claims, the singular forms "a," "an" and "the" include singular and/or plural reference unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 7. A) Nucleic acid sequence of the eyfp-gene and B) Nucleic acid sequence of a fragment of the eyfp-gene containing two close regions with high A and T percent composition indicated in bold selected for the gene editing study of the present disclosure.

DETAILED DESCRIPTION OF THIS DISCLOSURE

Figure 1:
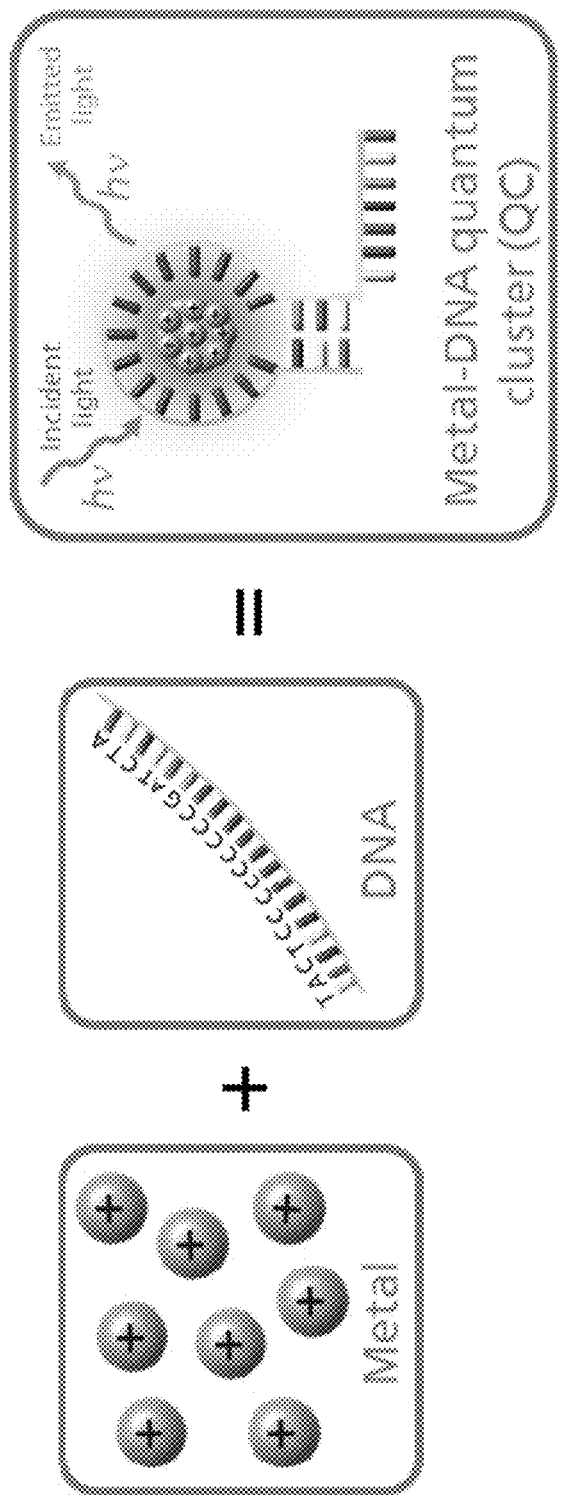
FIG. 1. Generation of metal-DNA quantum clusters (QCs) by the self-assembly of reduced metal atoms and DNA.
Figure 2:
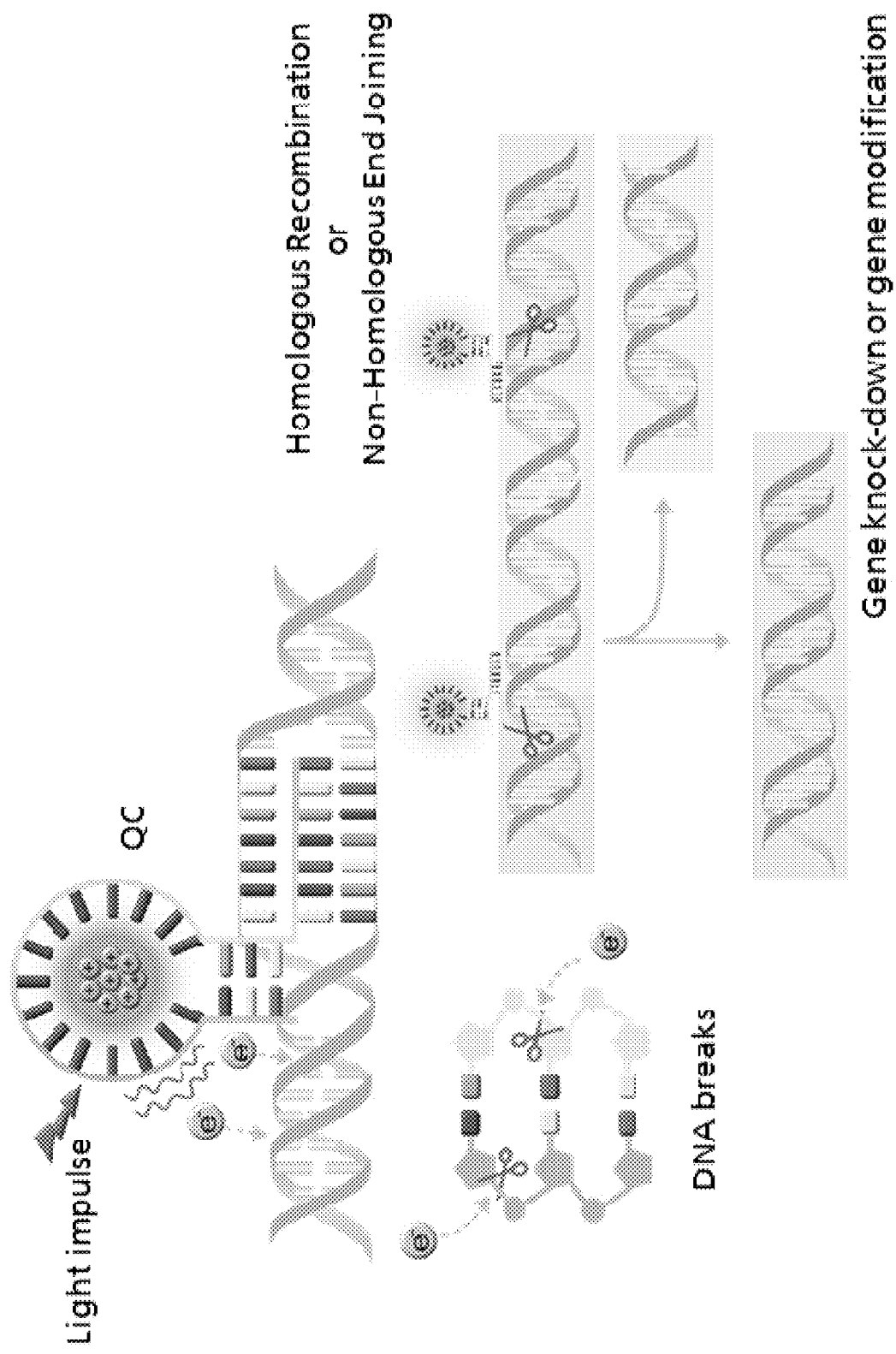
FIG. 2. Schematic representation of light-induced genome editing based on QCs. The diagram shows energy resonance effects and low-energy electron tunneling caused by an electromagnetic radiation hitting the QCs as an exemplary response able to induce DNA breaks at desired positions in the target DNA.

The present disclosure pertains to methods for modification/editing of a target DNA based on a combination of a cluster of metal atoms (e.g. <20 atoms), a nucleic acid like a DNA or RNA oligonucleotide that promotes the self-assembly of the cluster while folding around it and an electromagnetic radiation source, in particular a light source capable of exciting the electrons on the orbitals of the metal clusters at specific wavelengths or to induce a change in temperature of the metal nanocluster. The nucleic acid may include a short sequence of e.g. at least 10 base pairs long that can bind by e.g. complementarity to a target DNA or RNA sequence, e.g. encoding for a gene of interest to be modified. The methods aims to achieve a highly specific modification of genetic information encoded by nucleic acids including single and double stranded DNA and any type of RNA in vitro, in cell-free extracts or in vivo ideally in cells, organs and organisms including microorganisms, plants, animals or humans.

The methods of the present disclosure relates to methods for the modification of a target nucleic acid in vitro, ex vivo or in vivo in the genome of a cell comprising:
(i) providing a target nucleic acid sequence to be modified;
(ii) providing a pre-assembled complex comprising a nucleic acid and a metal nanocluster;
(iii) binding the complex to the target nucleic acid;
(iv) inducing one or more single or double stranded nucleic acid breaks in the target nucleic acid by exposing the complex bound to the target nucleic acid to electromagnetic radiation.

In some advantageous embodiments, the pre-assembled complex comprising a nucleic acid and a metal nanocluster are also called metal-DNA-quantum clusters (QC). The use of such QCs is central for the methods according to the present disclosure. In the prior art, such clusters are described e.g. as fluorescent nanocomposite tools in the literature that are suitable to several applications including among others the possibility to specifically recognize sequences on single stranded nucleic acids as reported in recent reviews (Tao Y., Li M., Ren J., Qu X. (2015) Metal nanoclusters: novel probes for diagnostic and therapeutic applications *Chem. Soc. Rev.* 44: 8636-8663/Liu J. J., Song X.-R., Wang Y.-W., Zheng A-X., Chen G. N., Yang H. H. (2012) Label-free and fluorescence turn-on aptasensor for protein detection via target-induced silver nanoclusters formation. *Anal. Chim. Acta* 749:70-74.). However, the use of QCs for genome editing has not been described yet.

The synthesis of the QCs has been described in the prior art (Petty J. T., Zheng J., Hud N. V., Dickson R. M. (2004) DNA-templated Ag nanocluster formation. *J. Am. Chem. Soc.* 126:5207-5212 and Vosch T., Antoku Y., Hsiang J. C., Richards C. I., Gonzalez J. I., Dickson R. M. (2007) 'Strongly emissive individual DNA-encapsulated Ag nanoclusters as single-molecule fluorophores', *Proc. Natl. Acad. Sci.* 104:12616-12621).

In particular, a "metal nanoclusters" in view of the present disclosure is a collection of small numbers (e.g., 2-30 atoms) of noble metal atoms (e.g., gold or silver atoms) with physical sizes close to the Fermi wavelength of an electron (about 0.5 nm for gold and silver). The metal atoms can have affinity for nitrogen atoms on DNA, including the N3 of cytosine and the N7 of guanine. In particular, the metal nanocluster in the complex according to the present disclosure comprises at least 2 atoms, more preferably 2 to 30 atoms and even more preferably 2 to 14 atoms".

In some advantageous embodiments, the metal nanocluster in the complex comprises at least 2 metal atoms. In particular, the metal nanocluster in the complex are a metal selected from the group consisting of transition metals including but not limited to noble metal atoms like silver, gold or platinum atoms, post transition metals including but not limited to gallium and thallium atoms, metalloids including but not limited to antimony and tellurium atoms, lanthanoids atoms including but not limited to lanthanum, terbium, ytterbium, gadolinium atoms, alkali metals including but not limited to cesium and rubidium atoms and or combinations of two or more elements belonging to any one of these metal classes.

In some advantageous embodiments, the resulting oligonucleotide-templated silver nanoclusters are a versatile set of fluorophores. They have been used for a variety of applications including live cell imaging, detection of specific metal ions, and single-nucleotide variation identification. These DNA/Ag NCs are very small, relatively simple to prepare, and show high or tunable biocompatibility. They have much better photostability than commonly used organic dyes and may also be a few times brighter. Unlike organic dyes and photoluminescent nanocrystals, they are subject to silver oxidation/reduction or nanocluster ("NC") regrouping, which results in conversion among different NC species. These different species may have different colors. The conversion amongst different NC species is not well understood, but may be reversible and depends on a number of factors including time, temperature, oxygen and salt content.

A "nucleic acid" is a deoxyribonucleotide or ribonucleotide polymer, which can include analogues of natural nucleotides that hybridize to nucleic acid molecules in a manner similar to naturally occurring nucleotides. In a particular example, a nucleic acid molecule is a single stranded (ss) DNA or RNA molecule, such as a probe or primer. In another particular example, a nucleic acid molecule is a double stranded (ds) nucleic acid, such as a target nucleic acid. Examples of modified nucleic acids are those with altered backbones, such as peptide nucleic acids. In particular, the nucleic acid comprised in the complex is DNA or RNA or a DNA-RNA hybrid or any other form of synthetic nucleic acid including but not limited to peptide nucleic acids (PNA), or locked nucleic acids (LNA), or threose nucleic acids (TNA), or glycol nucleic acids (GNA), or morpholinos, or derivative thereof. In particular, the target nucleic acid is DNA or RNA.

As used herein and mentioned above "genetic modification" or "altering the genome" or "modification of a target nucleic" means that a gene/nucleic acid sequence may be removed, or "knocked out" using a method according to the present disclosure. In particular, the present disclosure pertains to methods for modifying/editing in particular eukaryotic genomes like mammalian or plant genomes using non-transgenic strategies.

In some advantageous embodiments, the nucleic acids comprised in the complex includes at least one synthetic or naturally occurring nucleobase analogue within the sequence or at the 5' or 3' ends of the nucleic acid and suitable to any further chemical reaction for the purpose of functionalization of the nucleic acid.

In some advantageous embodiments, the nucleic acid in the complex comprises a) a nucleic acid sequence that is recognizing and binding to a sequence in the target nucleic acid and b) a nucleation sequence for the formation of the metal nanocluster. Therefore, the nucleic acid as part of the complex comprises a nucleotide sequence that can bind by e.g. base complementarity and thereby hybridizing with a portion of the nucleotide sequence of the DNA target, and a nucleotide sequence that comprises a metal nanocluster.

In particular, the nucleic acid comprised in the complex has a "nucleation sequence", i.e. a sequence of nucleotides capable of binding or associating with metal atoms to form template metal nanoclusters. The portion of a nucleic acid molecule including a nucleation sequence of nucleotides is referred to as the "nucleation portion" of the nucleic acid molecule. Exemplary nucleation sequences are known in the prior art. Specific nucleation sequences that are useful for interacting with metal nanoclusters and forming DNA templated metal nanoclusters are disclosed herein. As mentioned above, examples of metal nanoclusters for use as fluorescent reporters, and methods of producing templated metal nanoclusters on DNA oligonucleotides are known. See, e.g., U.S. Patent Publication No. US20110212540, and U.S. Patent Publication No. US20140349289.

In some embodiments, the nucleation sequence of the nucleic acid of the complex can fold into nucleic acid motifs including but not limited to at least one i-motif, or a g-quadruplex motif, or a g-motif or any other motif responsible for the formation of secondary structures in the nucleic acid that can act as nucleation sequences to support the formation of a metal nanocluster.

In some advantageous embodiments, the pre-assembled complex comprising a nucleic acid and a metal nanocluster is an isolated complex. An "isolated" complex (such as a QC) has been substantially separated, produced apart from, or purified away from other biological components. Nucleic acid molecules which have been "isolated" include nucleic acids molecules purified by standard purification methods, as well as those chemically synthesized. Isolated does not require absolute purity, and can include nucleic acid molecules that are at least 50% isolated, such as at least 75%, 80%, 90%, 95%, 98%, 99% or even 100% isolated.

As mentioned above, embodiments of the present disclosure pertains to methods for the modification of a target nucleic acid in vitro, or ex vivo or in vivo in the genome of a cell comprising:
(i) providing a target nucleic acid sequence to be modified;
(ii) providing a pre-assembled complex comprising a nucleic acid and a metal nanocluster; (hereafter referred to as the complex);
(iii) binding the complex to the target nucleic acid by hybridization or any other chemical interaction comprising but not limited to the formation of e.g. hydrogen bonds;
(iv) inducing one or more single or double stranded nucleic acid breaks in the target nucleic acid by exposing the complex bound to the target nucleic acid to electromagnetic radiation.

The methods according to the present disclosure are mainly based but not limited to quantum effects that may arise due to the intrinsic properties of the QCs to interact with electromagnetic radiation, in particular to fluoresce, i.e. to absorb photons from an external source of light and to emit these photons in the environment surrounding the clusters. In particular one aspect that should be taken into account is the property of these clusters to induce energy transfer by resonance effects which can result in energy transfer to the electrons of the DNA bases of the target gene when closely located to the QCs. The result is a sort of a cascade-like energy transfer to the bases of the nucleic acid of the target gene (or of a RNA transcript if the QCs are targeting RNA) that may destabilize the backbone of the nucleic acid thereby inducing formation of breaks between the phosphate and the sugar moiety of the nucleic acid. Ionizing radiations such as gamma-rays, X-rays or highly energetic short UV radiation have been reported to induce DNA breaks and are the foundation of radiotherapy in e.g. cancer patients or are the cause of spontaneous DNA mutations. These radiation may cause DNA breaks in an uncontrolled fashion and are therefore not suitable for the scope of this invention. Thus the electromagnetic radiation of the present invention does not include ionizing radiations. Our method can exploit but is not limited by these phenomena in order to induce DNA breaks by light pulse using the QCs when bound to specific regions of the gene of interest.

In some advantageous embodiments, the pre-assembled complex comprising a nucleic acid and a metal nanocluster binds to the target nucleic acid by hybridizing to a complementary sequence of the nucleotide sequence of the DNA target. Such a complementary binding of the complex occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bind to 3'-TAGC-5' of another ssDNA to form a dsDNA. In this example, the sequence 5'-ATCG-3' is the reverse complement of 3'-TAGC-5'. Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

The term "hybridization" is defined as the formation of base pairs between complementary regions of two strands of DNA, RNA, or between DNA and RNA, thereby generating a duplex molecule, for example. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

Typically, the part of the nucleic acid comprised in the complex nucleotide sequence that complements, and can hybridize with, a portion of the nucleotide sequence of the DNA target, include at least about 10 contiguous nucleotides, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 contiguous nucleotides, that are complementary to a target nucleic acid molecule, such as 20-70 nucleotides, 20-60 nucleotides, 20-50 nucleotides, 20-40 nucleotides, or 20-30 nucleotides. Probes can also be of a maximum length, for example no more than 20, 25, 35, 40, 50, 75 or 100 nucleotides in length. The specificity of a sequence typically increases with an increase in the number of complementary nucleotides on the complementary sequence. In particular, the nucleic acid in the complex comprises a minimum of 10 nucleotides in length, but is not limited to a maximum nucleotide sequence length.

In some advantageous embodiments, the nucleic acid sequence comprised in the nucleic acid of the complex and responsible of binding to the target DNA includes at least 5 continuous nucleotides that are complementary or specifically binding to a sequence within the target nucleic acid.

In some advantageous embodiments, the nucleic acid sequence comprised in the nucleic acid of the complex and responsible of binding to the target DNA may bind by triple helical structures in which instead of canonical purine/pyrimidine Watson-Crick hydrogen bonds also purine/purine and pyrimidine/purine Hoogsteen and reverse Hoogsteen hydrogen bonds are formed. The methods of the present invention include the design of oligonucleotides according to the rules described in the literature for formation of triple helical structures. The oligonucleotides can include base analogues in their sequence which are reported to promote the formation of triple helical structures.

To form metal nanoclusters on DNA, in some examples positively charged metal ions (e.g., Ag+ atoms) are first attached to ssDNA (e.g., cytosine nucleotides) spontaneously in solution. Then, a reductant (e.g., sodium borohydride) is added to reduce the charge of the atoms (e.g., Ag+ to Ag(0)), after which metal atom "clusters" will form. The ssDNA prevents the metal cluster "from growing out of control".

In some advantageous embodiments, the target nucleic acid is derived from or in the genome of a prokaryotic or an eukaryotic cell. Exemplary eukaryotic target nucleic acids that can be modified with the methods of the present disclosure may be mammal nucleic acids such as nucleic acid from a rodent, mouse, rat, rabbit, guinea pig, ungulate, horse, sheep, pig, goat, cow, cat, dog, primate, human or non-human primate. Plant DNA may also be modified according to the disclosure. For example, nucleic acids from *Arabidopsis thaliana*, maize, sorghum, oat, wheat, rice, canola, or soybean may be modified. It is further contemplated that target nucleic from/in other organisms such as algae, nematodes, insects (e.g., *Drosophila melanogaster*, mosquito, fruit fly, honey bee or spider), fish, reptiles, amphibians and yeast may be modified. In some advantageous embodiments, the target nucleic acid is in or derived from the genome of a plant cell, including but not limited to a cell from the Solanaceae family, like *Nicotiana tabacum* or *Nicotiana benthamiana*. In other embodiments, the cell is a human or animal cell, including but not limited to a cell from the group of tumor cells, stem cells and cells in any tissue or organ of a multicellular organism. In other embodiments, the target nucleotide sequence is in or derived from a virus.

Exemplary cell types in which the target nucleic acid can be modified with the method of the present disclosure include, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte.

A cell in which a target nucleic acid like DNA and/or RNA can be modified at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as those found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell, skin stem cell, epidermal stem cell, or follicular stem cell. Generally any type of stem cell can be modified including, without limitation, an embryonic stem cell, adult stem cell, totipotent stem cell or pluripotent stem cell.

However, if the cells are human embryonic stem cells (hESC), the hESC are derived from a human embryonic stem cell line wherein the human embryonic stem cell line has not been obtained by means of a process in which human embryos are destroyed. In some advantageous embodiments, the cells are induced pluripotent stem cells (also known as iPS cells or iPSCs) or a cell derived from a plutipotent cell like a iPS cell. In particular, the cell derived from a plutipotent cell is a differentiated cell.

In particular, the present disclosure pertains to the use of a method according to the present disclosure for genome engineering, provided that said use is not a method for treatment of the human or animal body by surgery or therapy, and provided that said use is not a process for modifying the germline genetic identity of human beings. In some advantageous embodiments, said genome engineering comprises modifying a target polynucleotide in a eukaryotic cell, modifying expression of a polynucleotide in a eukaryotic cell, generating a model eukaryotic cell comprising a mutated disease gene, or knocking out a gene.

In some advantageous embodiments, the method according to the present disclosure is not an in vivo application in animal. In some advantageous embodiments, the method according to the present disclosure is not a process of modifying the germ line genetic identity of human beings. In some advantageous embodiments, the cells are not derived from a human embryo.

In some advantageous embodiments, more than one pre-assembled complex comprising a nucleic acid of different sequence and a metal nanocluster is provided and bound to the target nucleic acid to induce one or more single or double stranded nucleic acid breaks at a different position in the target nucleic acid after exposing the complexes bound to the target nucleic acid to electromagnetic radiation.

In some advantageous embodiments, one or more single or double stranded nucleic acid breaks in the target nucleic acid are induced by exposing the complex bound to the target nucleic acid to electromagnetic radiation.

Examples for the electromagnetic radiation include but are not limited to near ultra violet, visible, near infrared, infrared wavelengths, or microwaves, or radio waves. In particular, the electromagnetic radiation is a non-ionizing radiation.

In some advantageous embodiments, the electromagnetic radiation originates from any emitting device selected from the group including but not limited to a mercury or xenon arc lamp, a metal halide arc lamp, a Light Emitting Diode (LED) or any Light Amplification Stimulated Emission Radiation device (LASER) including but not limited to solid state or gas lasers with continuous wavelength emission or pulsed emission covering a broad range of wavelengths from ultraviolet to infrared light, or a microwave or a radio wave source. In particular, the source of electromagnetic radiation is a continuous wave and/or pulsed laser or any pulsed source of radiation.

The methods according to the present disclosure, may be applied to several research areas and industrial applications including but not limited to genome editing of:
  plants/crops with the purpose of improving trait quality, e.g. their performance in biomass and raw material production for feed and food products or for production of energy;
  microorganisms to e.g. improve their performance in production of proteins including enzymes for biotechnological application or vaccines or antibodies for biomedical application or metabolites with relevant industrial application;
  animal or human cells for the purpose of dissecting biological pathways with extremely high relevance for understanding and fighting diseases or for correcting mutations that cause malfunction of cells and therefore induce pathological states.

The DNA cleavage is also relevant to biotechnology companies providing solutions for cell biology studies or for molecular biology applications such as e.g. elucidation of gene function, the possibility to achieve genetic manipulation of nucleic acids in vitro e.g. by replacing restriction enzymes and the limitations related to their usage in molecular cloning approaches.

These are only few examples to show the broad range of industrial applications in the life sciences that the technology may offer and which also include but is not limited to all the application relevant to the other current genome editing technologies.

Example 1—Synthesis of QCs

The synthesis of the QCs is carried out according to the following steps 1 to 15:
1. Identify an appropriate structure of the oligonucleotide for the synthesis of the QC such a linear or a stem-loop or a hairpin structure. In the example provided herein oligonucleotides with either a linear or a hairpin structure are selected (for sequence details see the points 2 and 3 below). However, the structure presented here is not to be considered limiting in that e.g. also a combination of two linear structures, two loops or a loop and a linear structure at both the 5' and 3' end of the oligonucleotide can be included. Additionally also loop structures within the oligonucleotide sequence can be included wherein the nucleation sequence of the QCs is in the middle of the oligonucleotide and the annealing regions are flanking upstream and downstream the nucleation sequence. In such a structure the nucleation sequence can either be a linear motif or be designed such as to include two complementary regions that upon folding of the QCs anneal to form a hairpin loop structure, wherein the annealing regions are located at the 5' and 3' side i.e. upstream and downstream of the hairpin loop nucleation sequence. Similar QC structures are known to those skilled in the art,
2. Select and design the DNA sequence of the QC including:
   a. a nucleation sequence composed of but not limited to preferentially cytosines or guanines (e.g. 3 up to 12 cytosines or guanines) which both have higher affinity for e.g. $Ag^+$ ions. For the purpose of the present invention the nucleation sequence can be designed following two strategies:
      i. the nucleation sequence is not present in the gene to be edited and can be composed preferentially of cytosine as mentioned above or a combination of cytosines and guanines or more complex motifs derived from e.g. nucleation sequences reported in the literature with defined fluorescence properties. In the example provided herein, the nucleation sequence is composed of 8 cytosines (refer to point c. below for sequence information). Additionally a sequence with a mixed composition of all the 4 nucleotides capable of producing bright and stable QCs is also included as an example (refer to point c. below).
      ii. The nucleation sequence is present in the gene of interest and is flanking the annealing region either at the 5' or 3' end. For this strategy it is important to consider the composition of the region flanking the annealing region so that different annealing regions and nucleation regions have to be tested to identify those combinations which result in synthesis of fluorescent QCs. An example of such a QC composition is provided below (see point c. QC_7).
   b. a DNA binding sequence based on the composition of the target nucleic acid in order to ensure binding of the QCs to the target nucleic acid by e.g. complementary base pairing and formation of hydrogen bonds. The DNA binding sequence should be preferably composed of adenines and/or thymines (A/T).

Thus, for the scope of the present invention A/T-rich sequences should be identified in the target gene. Ideally these A/T-rich sequences should not occur more than once in the gene of interest and possibly in the whole genome of the cell whose DNA is to be edited. Gene regions rich in A/T are identified using standard software for primer design wherein the length and the nucleotide composition in percent can be set as the selection criteria. For instance lengths of but not limited to 10 up to 20 bases with an A/T percent composition set but not limited to 60% threshold are iteratively screened on a target gene each time by changing the length of the oligonucleotides until sequences rich in A and/or T are identified. The length provided above is exemplary and should not be regarded as limiting because as long as the threshold in A/T percent composition is satisfied the target gene may also be screened using longer oligonucleotide lengths. Accordingly, also the percent of A/T occurrence can be set to a threshold of 30% up to 80%, more preferably 60% up to 70% and even more preferably to at least 60%. Following identification of A/T rich regions the final selection for the design of the annealing region composing the QCs should be based on proximity criteria meaning that gene regions are preferred wherein two or more A/T rich region are located next to each other e.g. separated by regions wherein the A/T composition falls below threshold of 60%. Gene regions showing two or more of such A/T-rich sequences are preferred because they may be suitable to anneal more QCs in close proximity to each other.

Figure 3:
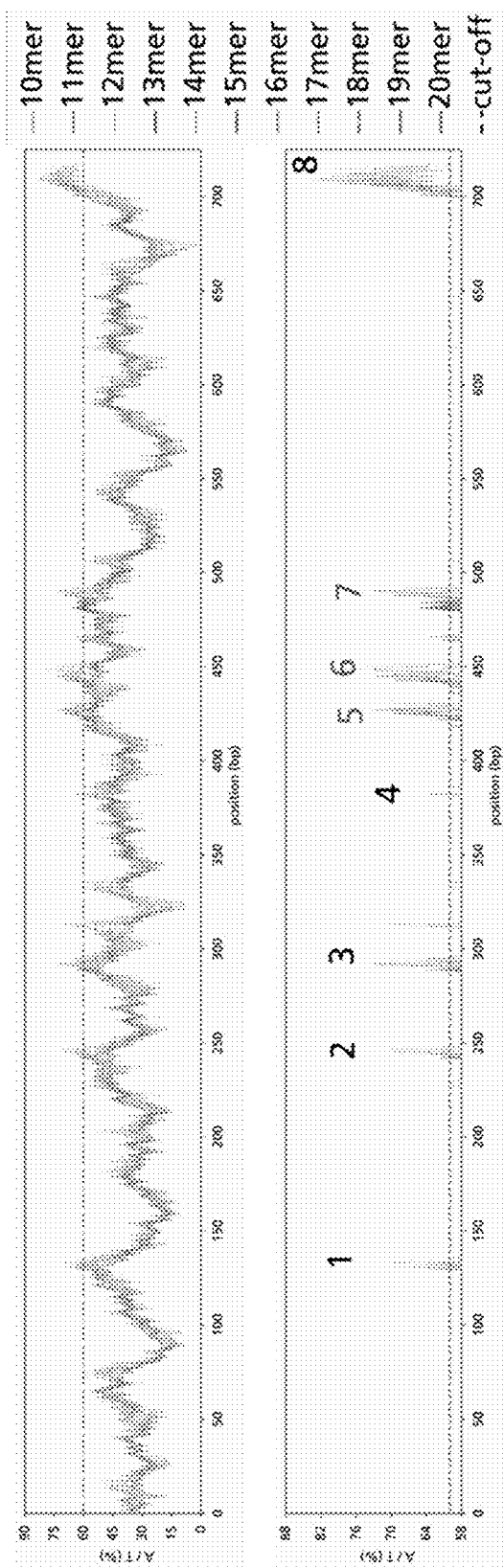
FIG. 3. Identification and selection of A/T rich regions within the eyfp gene by screening 10-mers up to 20-mers oligonucleotide sequences. Numbers in red indicate the A/T-rich regions selected for the design and synthesis of the QCs of the present invention.

In the example provided herein the target gene to be modified is the enhanced yellow fluorescent protein (eyfp) (SEQ ID NO. 12). For this gene, regions showing percent composition of A and/or T above a threshold set to 60% are shown in FIG. 3 (regions labeled with the numbering 1 to 8). The region selected for designing the annealing region of the QCs is located starting from nucleotide 365 up to nucleotide 514 of SEQ ID NO. 12 wherein the proximity criteria of two A/T rich regions are satisfied (regions highlighted in bold for SEQ ID NO. 13 and indicated with the number 5+6 and 7 in FIG. 3).

c. Based on the procedure described under point a and b several oligonucleotides are designed. For the eyfp gene example provided herein oligonucleotides selected according to the criteria of point a and b are listed in the table 1 and 2 below:

TABLE 1

Examples of QCs used in the present invention designed with metal templating regions (in bold) not belonging to the gene to be edited.

| Name | Structure | Sequence (5' > 3') |
|---|---|---|
| QC_1 | Linear | CCC CCC CCT GTT GTA GTT GTA CT |
| QC_2 | Hairpin loop | CAA TAT AT C CCC CCC CAT ATA TTG TGT TGT AGT TGT ACT |
| QC_3 | Linear | CCC CCC CCA TGA TAT AGA CGT TGT |
| QC_4 | Linear | CCC CCC CCA CAA CGT CTA TAT CAT |
| QC_5 | Hairpin loop | CAA TAT ATC CCC CCC CAT ATA TTG ACA ACG TCT ATA TCA T |
| QC_6 | Linear | GGG GCC TCT AAT GGG TAC CAT GCT TTG GAT GAT ATA GAC GTT GT |

TABLE 2

Example of QCs used in the present invention designed
with a metal templating region belonging to the gene to be edited
(in bold) and flanking the annealing region of the QC.

| Name | Structure | Sequence (5' > 3') |
|------|-----------|---------------------|
| QC_7 | Linear | G CCG TTC TTC TGC TTG TCG GCC ATG ATA TAG ACG TTG T |

3. Synthesize the oligonucleotide with the sequence determined under the above points 1. to 2. This is normally achieved by specialized companies which are offering a synthesis service and are able to deliver oligonucleotides with high purity and integrity. The latter requisites are very important for the success of the methods of the present invention.
4. Dissolve the oligonucleotide in nuclease-free sterile deionized water or buffer preferentially a buffer with neutral or slightly acidic or slightly alkaline pH (e.g. sodium phosphate buffer pH 7.0, 5 mM Tris-Cl pH 8.0) to a concentration of 100 or 500 µM.
5. Dilute the oligonucleotide to a suitable concentration (e.g. 20 µM) in nuclease-free water or buffer prepared with nuclease free water (e.g. sodium phosphate buffer or other buffer as mentioned above).
6. Select the concentration of the metal ion according to the length and composition of the oligonucleotide and in particular of the nucleation region of the oligonucleotide. Typically molar ratios of 1-2 moles metal per e.g. cytosine in the nucleation region are selected. More typically a general ratio of 6 up to 12 moles metal per mole of oligonucleotide is used. More preferably several ratios are to be tested in order to identify the most suitable for inducing formation of functional QCs. In general also some nucleotides of the annealing region may contribute to formation of the QC. This may be different for each oligonucleotide and should be tested case by case. In the example provided herein the molarity of the metal solution is calculated based on the full length of the oligonucleotide according to the following equation:

metal molarity=molar concentration of the oligonucleotide in solution×length of the oligonucleotide×desired metal to base molar ratio For instance to obtain a silver molar to base ratio of 0.3 for a 10 µM solution of an oligonucleotide composed of 24 bases the molarity of silver in solution should be calculated as follows: 24 bases×10 µmoles/base× 0.3 molar ratio=72 µmoles of silver.

Starting from e.g. 1 mM silver nitrate stock solution and for a reaction volume of 50 µL to achieve 72 µM solution the following volume of 1 mM silver nitrate should be added in the oligonucleotide solution: µL silver=72 µM×50 µL/1000 µM=3.6 µL.

In the example provided herein silver to base molar ratios of 0.2, 0.3, 0.4, 0.5, 0.6, 0.8 and 1 were tested in order to identify those that induce formation of the most fluorescent QCs. For the scope of the present invention QCs with preferred properties of fluoresce intensity and stability the best silver to base ratios ranged from 0.4 to 0.6.
7. Prepare a solution of metal ion (e.g. silver nitrate) in the selected concentration calculated according to the equation provided under point 6. Dissolve the metal ions in water or in the same buffer in which the oligonucleotide is dissolved. A buffer with neutral or slightly acidic pH is preferred such as but not limited to e.g. 5 mM sodium phosphate buffer pH 7.0 or 20 mM ammonium acetate buffer pH 6.9, or 30 mM Hepes 20 mM sodium acetate buffer pH 7.4 or 10 mM Tris-acetate buffer pH 8.0, or 30 mM Hepes 20 mM potassium acetate pH 7.4).
8. Mix the metal ion solution with the oligonucleotide by stirring for at least 15 minutes at room temperature. The reaction time between the metal atoms and the oligonucleotide is strictly dependent on the metal species (e.g. 15 minutes are sufficient for silver whereas several hours may be required for gold atoms).
9. Prepare a solution of a reducing agent. Typically the reducing agent is selected based on the metal ions. More typically the reducing agent is sodium borohydride. The reducing agent is freshly prepared each time in sterile nuclease-free deionized water or in the same buffer wherein the oligonucleotide and the metal ions are dissolved. Typically the concentration of the reducing agent is 1 mole per mole of metal.
10. Quickly add the reducing agent to the reaction mixture and stir at room temperature for at least 15 minutes. The length of the reaction is strictly dependent on the metal (see above point 8). Typically the reaction is carried out at room temperature or a 4° C. for 2 hours up to 24 hours. Reactions carried out at RT can be completed over night at 4° C.
11. Characterize the synthesized QCs by fluorescence spectroscopy to evaluate if the reaction has occurred successfully. The QCs should be excited by light of a specific wavelength and emit light of longer wavelength. The excitation and emission light should be determined for each assembled QC. For the example provided herein the fluorescence properties of the resulting QCs including the wavelength of maximum fluorescence excitation and emission is provided in table 3 below.

TABLE 3

Excitation (ex.) and emission (em.) maxima of QCs with different length composition and structure.

| Name | Sequence | ex. max. (nm) | em. max. (nm) |
|------|----------|---------------|---------------|
| QC_1 | CCC CCC CCT GTT GTA GTT GTA CT | 419 | 545 |
| QC_2 | CAA TAT AT C CCC CCC CAT ATA TTG TGT TGT AGT TGT ACT | 454 600 | 622 695 |
| QC_3 | CCC CCC CCA TGA TAT AGA CGT TGT | 437 | 541 |
| QC_4 | CCC CCC CCA CAA CGT CTA TAT CAT | 454 | 561 |
| QC_5 | CAA TAT ATC CCC CCC CAT ATA TTG ACA ACG TCT ATA TCA T | 515 | 605 |
| QC_6 | GGG GCC TCT AAT GGG TAC CAT GCT TTG GAT GAT ATA GAC GTT GT | 599 | 678 |
| QC_7 | G CCG TTC TTC TGC TTG TCG GCC ATG ATA TAG ACG TTG T | 448 540 | 558 634 |

12. Purify the QCs by dialysis, desalting or diafiltration using filter with appropriate molecular weight cut offs. Typically a MWCO of 3 kDa is suitable for the QCs described herein. Nevertheless filters of 1, 2 or larger kDa MWCO are required in accordance with the length and molecular weight of the oligonucleotides selected for the synthesis of the QCs. This step is required to almost completely remove unreacted reagents such as the metal ions and residues of the reducing agent and can be also used in order to exchange the buffer in which the QCs are synthesized. The filtration of the QCs is carried out based on the instructions provided by the manufacturer of the filters. In the example provided herein the QCs are purified using 3 kDa MWCO filters with membrane composed of polyethersulfone (PES). The membrane is pre-equilibrated with 400 µl of DNAse-free distilled water. The equilibration is performed by centrifuging the filter tubes for 10 minutes at 5,000 g. The QCs are brought to a volume of 100 µL with water or the same buffer used for the synthesis and are filtered at 5,000 g and room temperature or 4° C. in the equilibrated diafilters for 6-8 minutes. For purification purposes the QCs retained by the filter are resuspended in the same volume of water or buffer used for the synthesis and the centrifugation is repeated one or two times. To perform a buffer exchange the volume of QCs retained in the top part of the filter after centrifugation is measured, $1/10^{th}$ volume of the new buffer is added and the samples are centrifuged again at 5,000 g. This step is repeated by increasing each time the concentration of the new buffer until 100% concentration of the new buffer is achieved. In the example provided herein the buffer exchange is carried out by raising the concentration of the buffer in five steps wherein the QCs are diluted in a solution containing $1/10^{th}$, $1/5^{th}$, one half of the new buffer and lastly two times in pure buffer. Altogether these steps allow to fully exchange the buffer used for the synthesis of the QCs for a different buffer which is e.g. more suitable for annealing the QCs to the annealing sequence in the target gene.
13. Further purification of the QCs is dependent on the application. For the purpose of the present invention it is not required absolute purity of the QCs since the unreacted oligonucleotides will not respond to treatment with electromagnetic radiation.
14. Perform a final characterization of the purified oligonucleotide to confirm the fluorescence properties of the QCs. This allows to identify the most correct excitation light to which the QCs is going to be exposed in order to achieve formation of DNA breaks.
15. Store the QCs for up to 48 hours at 4° C. Beyond this storage time the QC may show instability and loss of fluorescence as a result of unfolding of the metal cluster. In general the most efficient performance of the QCs is obtained when they are freshly synthesized. However, depending on their stability QCs can be still used between 2 to 4 days from synthesis and exceptionally stable ones even after one week from synthesis. As a general rule it is recommended to check the fluorescence properties of the QCs prior to their use for gene editing.

Example 2—Use of QCs for Genome Editing In Vitro

Genome editing can be carried out in vitro on plasmids or linear DNA with the purpose of introducing single or double strand breaks at a desired position in the sequence of the target DNA for e.g. further cloning or sub-cloning steps.

The editing of nucleic acid sequences in vitro is performed according to the following steps:
1. Selection of a target nucleic acid sequence to be modified. This is carefully performed in order to identify a sequence which is occurring only one time in the nucleic acid to be edited. The sequence in the nucleic acid should not contain a long stretch of cytosines or guanines and should preferentially contain abundant adenine and thymine. The guidelines for selecting a target sequence including the annealing region where the QCS are hybridizing to have been described under Example 1.
2. The selected region of the target nucleic acid is providing sequence information for the design of the DNA binding region of the QC. The design of the oligonucleotides and the synthesis of the QCs are carried out according to the procedure described under Example 1.
3. Purify and characterize the QCs according to the guidelines provided under Example 1.
4. The purified QCs are then mixed with the plasmid DNA or a linearized portion of the gene of interest in several molar ratios e.g. 1 mole QCs to 1 mole target DNA or e.g. 100 moles QCs to 1 mole target DNA both dissolved into an appropriate buffer (e.g. Tris-EDTA buffer). In general a large molar excess of the QCs with respect to the target DNA is preferred.

For the example provided herein a portion of the eyfp gene (refer to SEQ ID NO. 13) is amplified by PCR starting from the full length gene or from a gene fragment artificially synthesized and using the following primers with and without biotinylation at the 5' end.
Reverse primers:
Yf_r_641-5'-TCACCTTGATGCCGTTC-3'
Yf_r_641-B    5'-/Bio/TCACCTTGATGCCGTTC-3' (Bio=biotin)
Forward primers:
Yf_f_545-5'-GAGGACGGCAACATCCTG-3'
Yf_f_545-B  5'-/Bio/GAGGACGGCAACATCCTG-3' (Bio=biotin)
The PCR conditions are provided below:

| Initial | | | |
|---|---|---|---|
| denaturation | 98° C. | 10 sec | |
| Ddenaturation | 98° C. | 1 sec | |
| Annealing | 56° C. | 2 sec | ×25 cycles |
| Extension | 72° C. | 1 sec | |
| Final extension | 72° C. | 2 sec | |
| Cooling | 4° C. | hold | |

Figure 4:
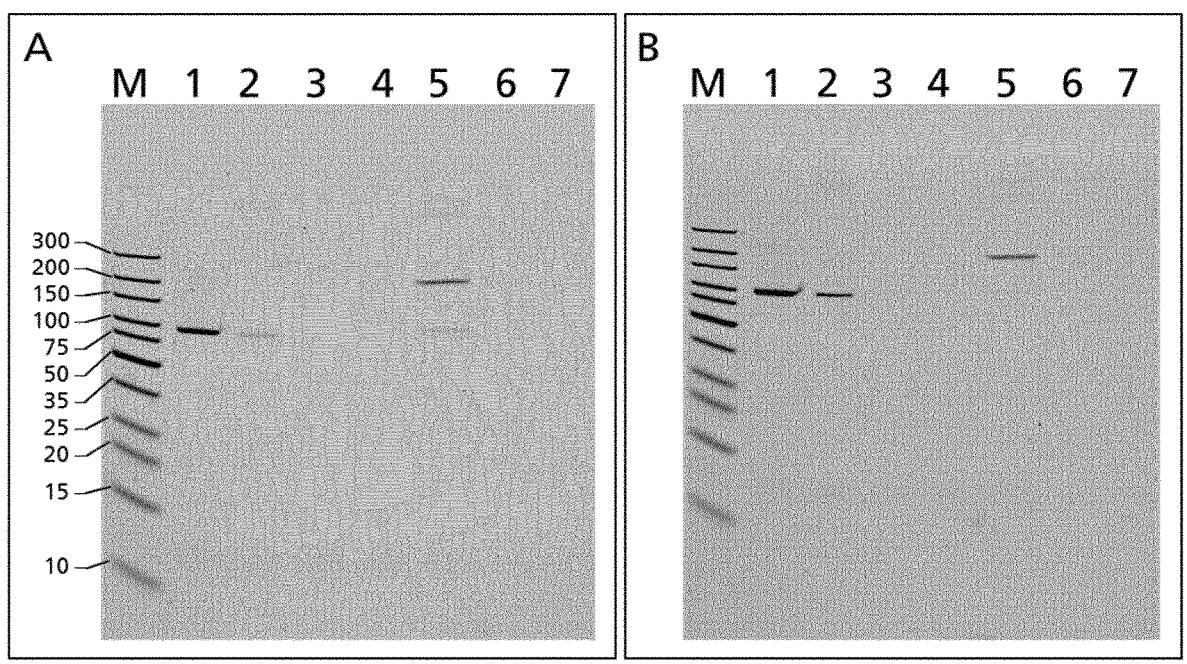
FIG. 4. Gel electrophoresis analysis of the isolation of a single stranded eyfp gene fragment by streptavidin-biotin mediated magnetic separation. A) Isolation of the single-stranded gene fragment in forward orientation; B) isolation of the single-stranded gene fragment in reverse orientation. M=Ultra-low range marker; 1=unbound double-stranded eyfp gene fragment; 2-4=first, second and third wash fraction after streptavidin-biotin capturing; 5-7=first, second and third denaturation and wash fraction showing release of non-biotinylated single-stranded eyfp DNA.

The polymerase is high fidelity Q5 polymerase (New England biolabs), the amount of template for each reaction is 10 pg and the concentration of the primer is 10 pmoles. Following PCR amplification the double stranded DNA with biotinylated forward or reverse strand is bound to streptavidin coated magnetic beads according to a standard protocol well-known to those skilled in the art. Following binding several washing steps are carried out to remove unbound DNA. Thereafter the bound gene fragment is treated two times for 2 minutes with a solution of 0.2 M sodium hydroxide (NaOH) in order to denature the DNA. By magnetic separation it is possible to keep only one DNA strand on the beads and to remove the non-biotinylated complementary strand. A third denaturing/washing step using 0.1 M NaOH and several washing steps using buffers recommend by the manufacturer of the beads are also included to remove residual non biotinylated single stranded DNA. The efficiency of binding of the biotinylated gene fragment to the streptavidin coated magnetic beads is then confirmed by gel electrophoresis using a standard protocol. For the example provided herein the results of the binding and recovery efficiency of single stranded DNA is shown in FIG. 4 for both the forward and reverse strand (panel A and B).

5. The single stranded DNA is thereafter employed to confirm binding of the QCs to the target DNA sequence using standard annealing protocols. Depending on the selected binding procedure it will be e.g. necessary to previously fully denature the plasmid DNA or the linear DNA containing the target nucleic acid sequence to be edited. This is achieved by incubating the plasmid or the linear target DNA at 95° C. for at least 5 minutes. Thereafter the DNA is rapidly cooled down to 4° C. The QCs pre-equilibrated at 4° C. are added to the target DNA solution. Additionally, in the example provided herein a linear single-stranded DNA bound to streptavidin coated magnetic beads and obtained by alkaline denaturation and magnetic separation as described above can be used to bind QCs to a portion of the target gene.

Figure 5:
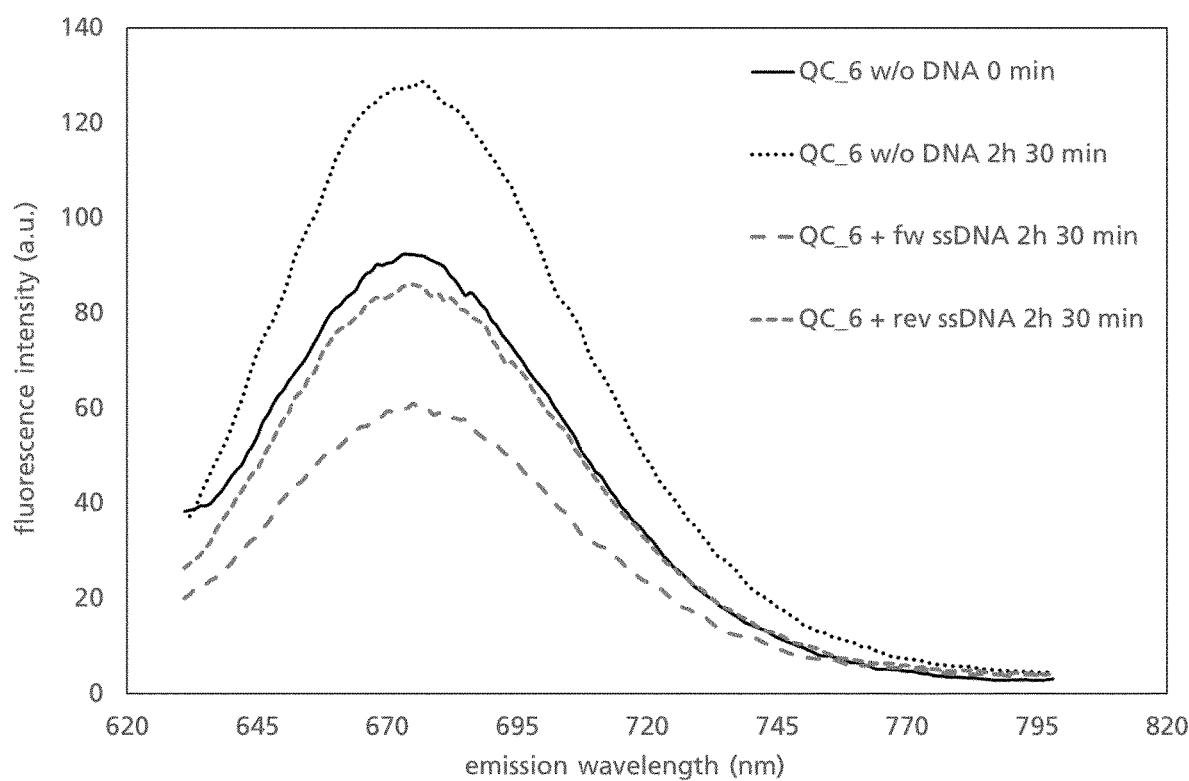
FIG. 5. Fluorescence spectroscopy analysis of binding studies of the quantum cluster QC_6 to a target single-stranded eyfp gene fragment (ssDNA). The curves represent emission spectra obtained at maximum excitation wavelength for QC_6 incubated without DNA or with single stranded DNA in forward (fw) or reverse (rev) orientation immobilized on magnetic beads after 2 hour and 30 minutes incubation under controlled temperature conditions. Decay in fluorescence of QC_6+fw ssDNA as compared to the reference signal of QC_6 w/o DNA at 0 min or after 2 hours 30 minutes incubation provides indication of binding of the QC to the target gene.
Figure 6:
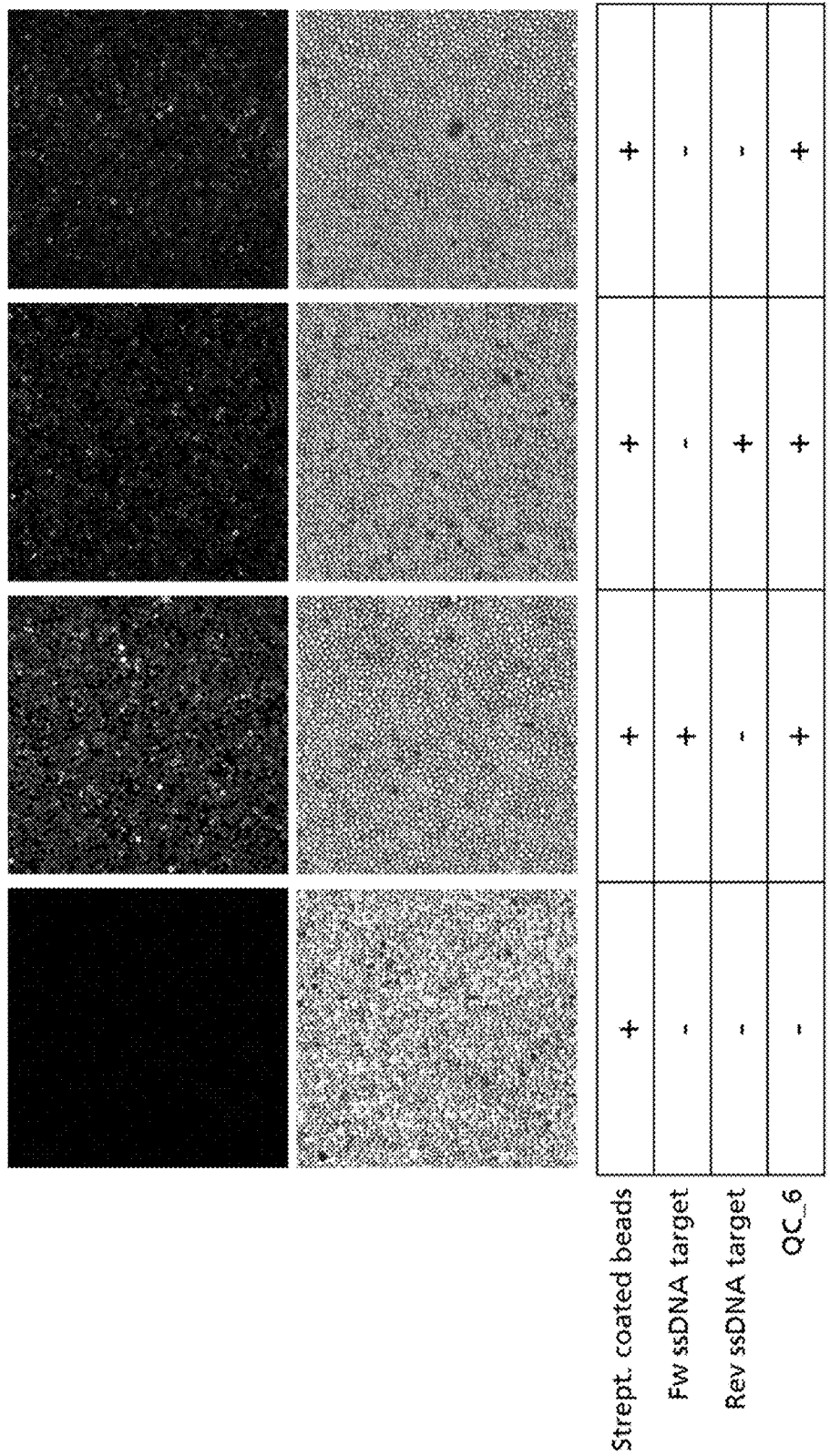
FIG. 6. Fluorescence microscopy analysis of QC binding. Upper panels are fluorescence confocal microscopy images of streptavidin coated beads with and without immobilized forward (Fw) or reverse (Rev) strand and acquired after incubation for 2 hours and 30 minutes in the presence or absence of QC_6. Lower panels are transmission light images. Control beads w/o ssDNA and without QCs were analyzed in order to exclude intrinsic autofluorescence of the beads under the irradiation conditions used throughout this experiment.

6. The resulting mixture composed of the plasmid DNA and the QCs is incubated at RT for 10 minutes to promote annealing of the DNA-binding region of the QCs to the target nucleic acid to be edited. Higher binding specificity of the QCs to the target gene can be achieved using appropriate buffers such as 30 mM Hepes buffer containing sodium or potassium acetate preferably with a concentration of but not limited to 20 mM salt. In the example provided herein the single-stranded target DNA bound to magnetic beads in the buffer above is incubated on ice for at least 10 minutes. The samples are then moved to a programmable thermostatic shaker set to a temperature of 60° C. and incubated for 8 minutes to favor dissociation of secondary structures due to self-annealing of the single stranded DNA. After this preliminary incubation the QCs is added to the bead suspension containing the single stranded target DNA of the gene and the temperature control of the shaker is set to 38° C. This way the suspension of the target gene and the QCs cools slowly down with a gradient of approx. 1° C. per minute until the goal temperature of 38° C. is reached. The QCs and the single-stranded DNA are further incubated under shaking at 38° C. for additional 2 to 3 hours. Thereafter the beads with the coated single-stranded DNA are removed from solution using magnetic separation. The residual fluorescence intensity of the solution deprived of beads is measured using a fluorimeter and is compared to the fluorescence intensity of a reference solution of the QCs without the beads and the target DNA treated under the same conditions. In the example provided herein the QC_6 (refer to Table 1 and 2 for sequence and fluorescence properties) is annealed to the forward single stranded DNA and for control also to the reverse single-stranded DNA to which the QCs should not bind to. The result of this analysis are shown in FIGS. 5 and 6. By a sharp decrease or quenching of fluorescence signal of the QC_6 in solution as compared to the reference solution w/o the target DNA and to the solution annealed to the reverse single stranded DNA it is possible to show that the QC is binding to the target gene with a good degree of specificity. Confirmation studies can be carried out using fluorescence microscopy whereby after completion of the binding studies 2 µL of beads with immobilized single-stranded target DNA and hybridized with the QCs are pipetted onto a microscopy grade glass slide and imaged using excitation and emission wavelength corresponding to the excitation and emission maxima of the QCs. For QC_6 of the present example a white light laser with tunable fluorescence excitation light is set to 599 nm. The irradiated beads are imaged with a high sensitive photomultiplier detectors in front of which tunable emission filters are set so as to cover the emission spectrum of the QC in the range corresponding to the highest emission fluorescence intensity. The result of the fluorescence microscopy analysis of beads coated with single stranded forward or reverse target DNA after incubation for 2 hours and 30 minutes with or without the QC_6 are shown in FIG. 6. Control samples consisting of beads without coating of single stranded DNA in the presence or absence of the QC_6 are also imaged in order to exclude artifacts due to autofluorescence of the beads or to unspecific binding of the QCs to the surface of the beads. In order to compare the intensity of the signals of the different bead samples all the images are to be acquired using the same settings for laser intensity and for the gain of the photomultiplier detectors.

7. The solution of QCs and the target DNA is then exposed to electromagnetic radiation (ER). The wavelength of the ER is selected based on the absorbance and emission properties of the QCs. Typically the electromagnetic radiation is in the visible or near infrared or infrared range. More typically the electromagnetic radiation is produced by a laser and more specifically by a multiphoton laser capable of high frequency pulsing. For the example provided herein the QCs are irradiated using either laser light of the specific excitation wavelength of the QCs (in the case of QC_6 this was set to 599 nm) or by using a femtoseconds pulsing multiphoton laser and exploiting dual photon excitation of the QCs with photons of longer wavelength (in the specific case of QC_6 the excitation was set to a wavelength of approx. 1040 nm).

8. The complex composed of the target nucleic acid and of the QCs will be hit by several irradiation rounds with electromagnetic radiation. The length of the ER treatment is determined each time for each target DNA and QCs combination. Typically the exposure to ER should be selected as to prevent spontaneous formation of uncontrolled DNA breaks. Therefore, it is always necessary to include control samples where the target DNA without QCs is exposed to the same irradiation conditions used for the samples where the QCs are annealed to the target DNA.

9. After exposure to ER the target DNA is analyzed in order to verify formation of the DNA breaks. This is achieved by several techniques including e.g. gel electrophoresis, PCR (e.g. rolling circle PCR for plasmid DNA) or sensitive analytical chromatographic separation.

10. The break is then also confirmed by sequencing the target DNA.

Example 3—Use of QCs for Genome Editing in Cells

Genome editing can be carried out in cells on genomic DNA with the purpose to ablate the function of undesired genes which are responsible for poor performance of e.g. crops or for studying the function of genes in cells of e.g. human origin in order to dissect the molecular mechanisms underlying a signaling pathway responsible for the onset of a disease.

The editing of nucleic acids in cells implicates the following steps:

1. Selection of a target nucleic acid sequence to be modified. This sequence should occur only one time in the haploid genome of the host cell. As indicated above the sequence in the nucleic acid should not contain a long stretch of cytosines or guanines and should preferentially contain abundant adenine and thymine. The guidelines for selecting a target sequence including the annealing region where the QCs are hybridizing to have been described above under Example 1.
2. The selected region of the target nucleic acid is providing sequence information for the design of the DNA binding region of the QC. The design of the oligonucleotides and the synthesis of the QCs are carried out according to the procedure described under Example 1.
3. The synthesized and purified QCs are diluted into a buffer compatible with the cultivation of cells e.g. phosphate buffer saline (PBS) or cell growth medium. Alternatively the synthesis of the QCs can be directly carried out in the buffer or medium.
4. The QCs is mixed to the cells in relatively high molar excess with respect to the target DNA. This is done to ensure homogeneous distribution of the QCs in the cells that need to be modified and to counteract possible degradation of the QCs by endogenous nucleases.
5. If penetration of the QCs across the cell membrane is not occurring spontaneously, the QCs will be introduced by other approaches including e.g. transfection. If the cell is a plant cell, than it might be necessary to digest the cell wall by any method described in the literature. This is achieved by means of e.g. commercially available digestion solutions containing e.g. macerozyme and cellulases. Thereafter the resulting protoplasts are incubated with the QCs to promote their penetration. If this cannot be achieved spontaneously the protoplasts are transfected by e.g. using poly(ethylene)glycol PEG according to well-established transfection protocols.
6. Following penetration the QCs are incubated with the cells for a few up to 24 hours. The incubation time has to be determined each time depending on the cell type to be treated.
7. The cells treated with the QCs are exposed to ER for inducing double strand breaks in the genome of the host cells. This require setting of preliminary control experiments to verify the susceptibility of the cells to treatment with ER. It is to be verified for each case the intensity and duration of the ER which does not induce damage (e.g. double strand breaks) beyond the natural rate of DNA damage and spontaneous mutation of the host cells.
8. After treatment with the QCs and ER the cells are subjected to several analyses to verify the occurrence of mutations in the target gene of interest. For instance if the mutation of the target gene in a plant cell induces a phenotypic change (e.g. an albino mutant) several regenerated plantlets are screened to identify the mutated phenotype. The genomic DNA extracted from these plantlets is then subject to analysis by PCR with selected primers targeting the gene of interest and by NG sequencing to verify the mutation and to exclude that off-target mutations may have been generated by the QCs after irradiation.

The invention claimed is:

1. A method of breaking a target nucleic acid in vitro, the method comprising:
(i) providing, in vitro, a target nucleic acid sequence comprising plasmid or linear DNA to be broken;
(ii) providing a pre-assembled complex for breaking the target nucleic acid sequence, the complex comprising:
   a. a metal nanocluster of 2 to 14 silver atoms;
   b. a nucleic acid molecule of single stranded DNA that is different from the target nucleic acid sequence and shorter than the target nucleic acid sequence, the single stranded DNA comprising:
      i. an annealing region of 10 to 25 consecutive nucleotides that comprises 60% adenine and thymine nucleotides that are complementary to consecutive nucleotides of the target nucleic acid sequence, and
      ii. a nucleation region that flanks the annealing region and is positioned around the metal nanocluster, the nucleation region comprising 8 consecutive cytosine nucleotides;
(iii) contacting the consecutive nucleotides of the annealing region of the complex to the consecutive nucleotides of the target nucleic acid, thereby annealing the pre-assembled complex to the target nucleic acid sequence; and
(iv) inducing a nucleic acid break in the target nucleic acid by exposing the metal nanocluster at the nucleation region to electromagnetic radiation.

2. The method according to claim 1, wherein the electromagnetic radiation is emitted as a wavelength selected from the group consisting of a visible wavelength, a near infrared wavelength, and an infrared wavelength.

3. The method according to claim 1, wherein the electromagnetic radiation is a continuous wave or a pulsed emission.

4. The method according to claim 1, wherein the nucleic acid molecule comprises a hairpin loop.

5. The method according to claim 1, wherein the target nucleic acid sequence comprises DNA obtained from human or plant.

* * * * *

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: QC Linear

<400> SEQUENCE: 1 ccccccctg ttgtagttgt act                                        23

<210> SEQ ID NO 2
<211> LENGTH: 39
<212> TYPE: DNA
<213> ORGANISM: Artificial Sequence
<220> FEATURE:
<223> OTHER INFORMATION: QC Hairpin loop

<400> SEQUENCE: 2
caatatatcc cccccatat attgtgttgt agttgtact                       39

<210> SEQ ID NO 3
<211> LENGTH: 24
<212> TYPE: DNA
<213> ORGANISM: Artificial Sequence
<220> FEATURE:
<223> OTHER INFORMATION: QC Linear

<400> SEQUENCE: 3
ccccccccat gatatagacg ttgt                                      24
```

<210> SEQ ID NO 4
<211> LENGTH: 24
<212> TYPE: DNA
<213> ORGANISM: Artificial Sequence
<220> FEATURE:
<223> OTHER INFORMATION: QC Linear

<400> SEQUENCE: 4 cccccccccac aacgtctata tcat                                   24

<210> SEQ ID NO 5
<211> LENGTH: 40
<212> TYPE: DNA
<213> ORGANISM: Artificial Sequence
<220> FEATURE:
<223> OTHER INFORMATION: QC Hairpin loop

<400> SEQUENCE: 5
caatatatcc cccccatat attgacaacg tctatatcat                    40

<210> SEQ ID NO 6
<211> LENGTH: 44
<212> TYPE: DNA
<213> ORGANISM: Artificial Sequence
<220> FEATURE:
<223> OTHER INFORMATION: QC Linear

<400> SEQUENCE: 6
ggggcctcta atgggtacca tgctttggat gatatagacg ttgt              44

<210> SEQ ID NO 7
<211> LENGTH: 38
<212> TYPE: DNA
<213> ORGANISM: Artificial Sequence
<220> FEATURE:
<223> OTHER INFORMATION: QC Linear

<400> SEQUENCE: 7
gccgttcttc tgcttgtcgg ccatgatata gacgttgt                     38

<210> SEQ ID NO 8
<211> LENGTH: 17
<212> TYPE: DNA
<213> ORGANISM: Artificial Sequence
<220> FEATURE:
<223> OTHER INFORMATION: Reverse Primer

<400> SEQUENCE: 8
tcaccttgat gccgttc                                            17

<210> SEQ ID NO 9
<211> LENGTH: 17
<212> TYPE: DNA
<213> ORGANISM: Artificial Sequence
<220> FEATURE:
<223> OTHER INFORMATION: Reverse Primer

<400> SEQUENCE: 9
tcaccttgat gccgttc                                            17

<210> SEQ ID NO 10
<211> LENGTH: 18
<212> TYPE: DNA
<213> ORGANISM: Artificial Sequence
<220> FEATURE:
<223> OTHER INFORMATION: Forward primer

<400> SEQUENCE: 10
gaggacggca acatcctg                                                   18

<210> SEQ ID NO 11
<211> LENGTH: 18
<212> TYPE: DNA
<213> ORGANISM: Artificial Sequence
<220> FEATURE:
<223> OTHER INFORMATION: Forward Primer

<400> SEQUENCE: 11
gaggacggca acatcctg                                                   18

<210> SEQ ID NO 12
<211> LENGTH: 720
<212> TYPE: DNA
<213> ORGANISM: Aequorea victoria

<400> SEQUENCE: 12
gtgagcaagg gcgaggagct gttcaccggg gtggtgccca tcctggtcga gctggacggc     60
gacgtaaacg gccacaagtt cagcgtgtcc ggcgagggcg agggcgatgc cacctacggc    120
aagctgaccc tgaagttcat ctgcaccacc ggcaagctgc ccgtgccctg gcccaccctc    180
gtgaccacct tcggctacgg cctgcagtgc ttcgcccgct accccgacca catgaagcag    240
cacgacttct tcaagtccgc catgcccgaa ggctacgtcc aggagcgcac catcttcttc    300
aaggacgacg gcaactacaa gacccgcgcc gaggtgaagt tcgagggcga cacccctggtg   360 aaccgcatcg agctgaaggg catcgacttc aaggaggacg gcaacatcct ggggcacaag    420
ctggagtaca actacaacag ccacaacgtc tatatcatgg ccgacaagca agaaaacggc    480
atcaaggtga acttcaagat ccgccacaac atcgaggacg gcagcgtgca gctcgccgac    540
cactaccagc agaacacccc catcggcgac ggccccgtgc tgctgcccga caaccactac    600
ctgagctacc agtccgccct gagcaaagac cccaacgaga gcgcgatca catggtcctg     660 ctggagttcg tgaccgccgc cgggatcact ctcggcatgg acgagctgta caagtaataa    720

<210> SEQ ID NO 13
<211> LENGTH: 150
<212> TYPE: DNA
<213> ORGANISM: Aequorea victoria

<400> SEQUENCE: 13
gcatcgagct gaagggcatc gacttcaagg aggacggcaa catcctgggg cacaagctgg     60
agtacaacta acagccac aacgtctata tcatggccga caagcagaag aacggcatca    120
aggtgaactt caagatccgc cacaacatcg                                    150